United States Patent
Schläpfer

(10) Patent No.: US 8,075,600 B2
(45) Date of Patent: Dec. 13, 2011

(54) DEVICE FOR THE DYNAMIC FIXATION OF BONES

(75) Inventor: Fridolin Schläpfer, Hölstein (CH)

(73) Assignee: Synthes USA, LLC, West Chester, PA (US)

( * ) Notice: Subject to any disclaimer, the term of this patent is extended or adjusted under 35 U.S.C. 154(b) by 788 days.

(21) Appl. No.: 11/653,329

(22) Filed: Jan. 12, 2007

(65) Prior Publication Data

US 2007/0233087 A1 Oct. 4, 2007

Related U.S. Application Data

(63) Continuation of application No. PCT/CH2004/000443, filed on Jul. 12, 2004.

(51) Int. Cl.
*A61B 17/70* (2006.01)

(52) U.S. Cl. .......... 606/266; 606/269; 606/272

(58) Field of Classification Search .......... 606/246, 606/264–279; 411/396, 380, 401; 403/76, 403/77
See application file for complete search history.

(56) References Cited

U.S. PATENT DOCUMENTS

| | | | |
|---|---|---|---|
| 5,057,111 A | 10/1991 | Park | |
| 5,480,401 A | 1/1996 | Navas | |
| 5,797,911 A | 8/1998 | Sherman et al. | |
| 5,879,350 A | 3/1999 | Sherman et al. | |
| 5,882,350 A * | 3/1999 | Ralph et al. | 606/278 |
| 5,885,286 A | 3/1999 | Sherman et al. | |
| 6,022,350 A | 2/2000 | Ganem | |
| 6,053,917 A | 4/2000 | Sherman et al. | |
| 6,063,090 A | 5/2000 | Schläpfer | |
| 6,132,432 A * | 10/2000 | Richelsoph | 606/278 |
| 6,280,442 B1 * | 8/2001 | Barker et al. | 606/60 |
| 7,144,396 B2 * | 12/2006 | Shluzas | 606/266 |
| 7,615,076 B2 * | 11/2009 | Cauthen et al. | 606/279 |
| 2005/0203516 A1 * | 9/2005 | Biedermann et al. | 606/61 |
| 2005/0216000 A1 * | 9/2005 | Colleran et al. | 606/61 |
| 2005/0228382 A1 * | 10/2005 | Richelsoph et al. | 606/61 |

FOREIGN PATENT DOCUMENTS

| | | |
|---|---|---|
| EP | 0 669 109 | 8/1995 |
| EP | 1 210 914 | 6/2002 |
| WO | WO 94/00066 | 1/1994 |
| WO | WO 98/25534 | 6/1998 |
| WO | WO 98/52482 | 11/1998 |
| WO | WO 2006/089292 | 8/2006 |

OTHER PUBLICATIONS

"Nitinol," Fort Wayne Metals, pp. 1-3, www.fortwaynemetals.com/specsheet_pdfs/nitinol.pdf, accessed Jul. 2, 2009.* Adams et al. "Effect of Molecular Structure on the Linear Viscoelastic Behavior of Polyethylene," 2000, Macromolecues, 33, 7489-7499.*
Polyethylene techanical Information, 2010, Landscapeforms, http://www.landscapeforms.com/en-US/LFI%20Material%20Tech%20Sheets/LFI_Polyethylene_Tech_2_10.pdf. accessed Jul. 13, 2010.*

* cited by examiner

*Primary Examiner* — Eduardo C Robert
*Assistant Examiner* — Steven Cotroneo
(74) *Attorney, Agent, or Firm* — Stradley, Ronon, Stevens & Young LLP

(57) ABSTRACT

An intermediate element for a detachable, lockable, ball joint-like connection in a device for the dynamic fixation of bones has a longitudinal axis, an outer wall concentric with the longitudinal axis, and an inner wall forming a coaxial cavity. Either the outer wall or the inner wall comprises one of two contact zones that form the ball joint-like connection. The intermediate element is at least partly made of a super-elastic or visco-elastic material.

35 Claims, 7 Drawing Sheets

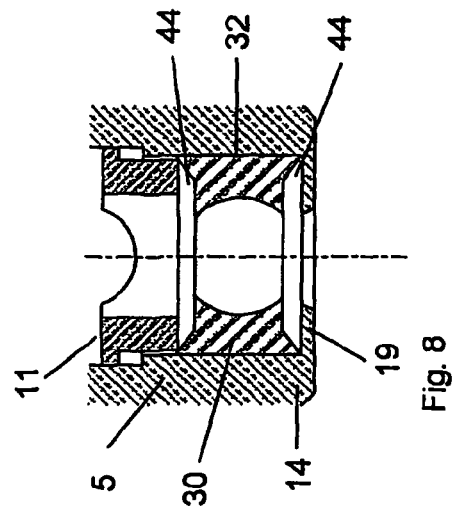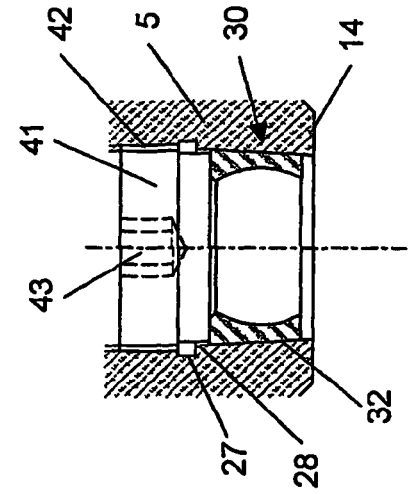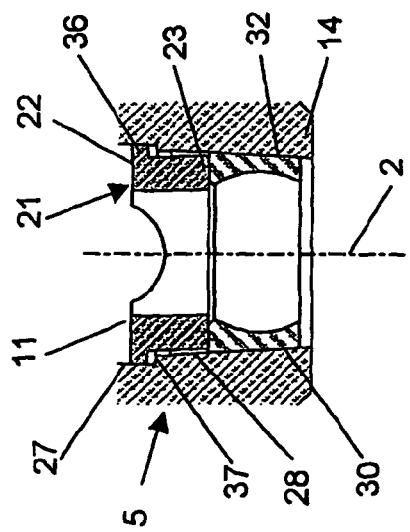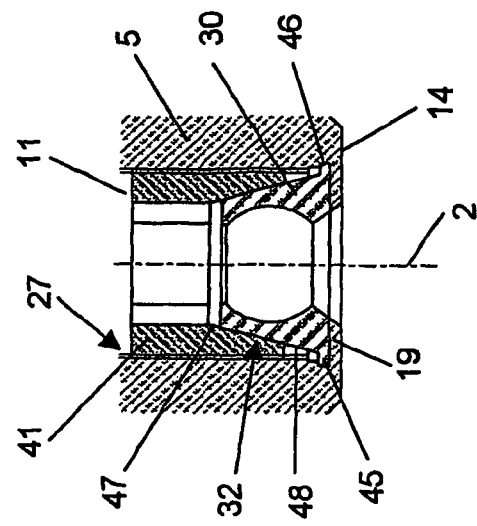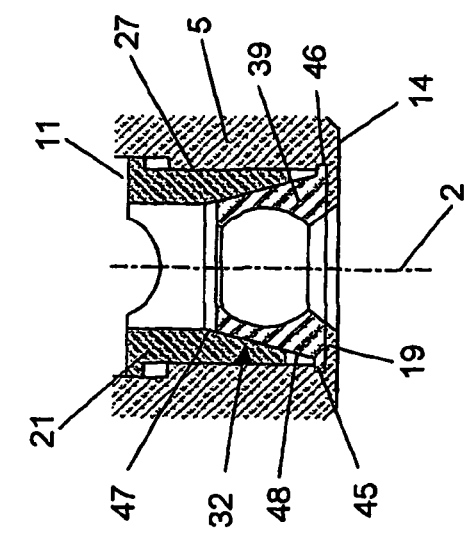

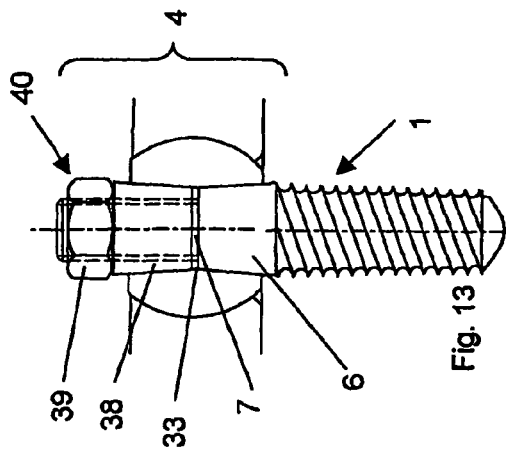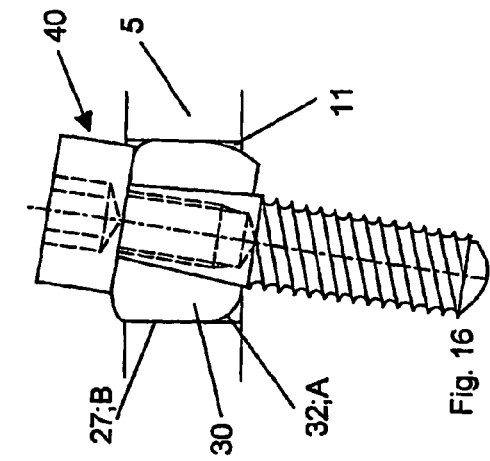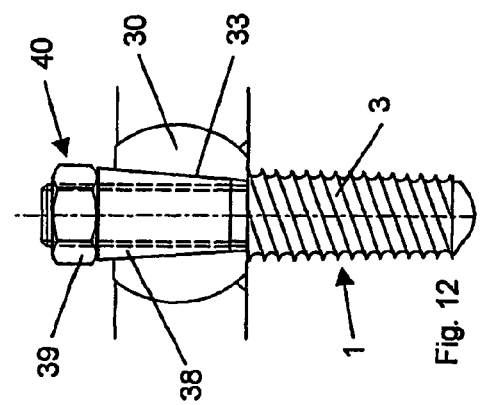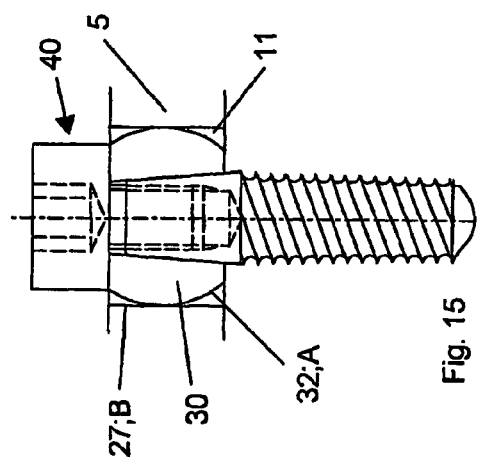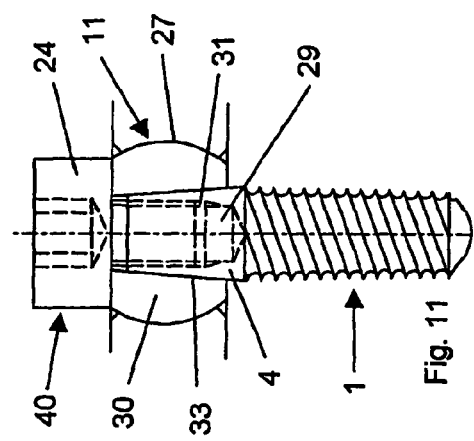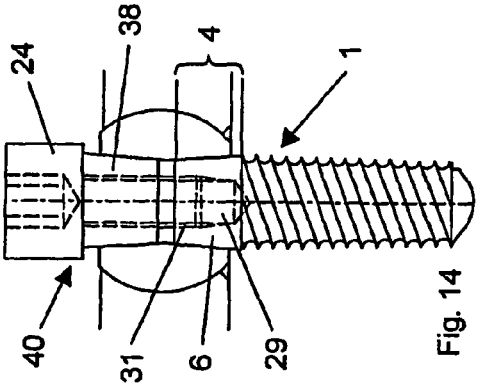

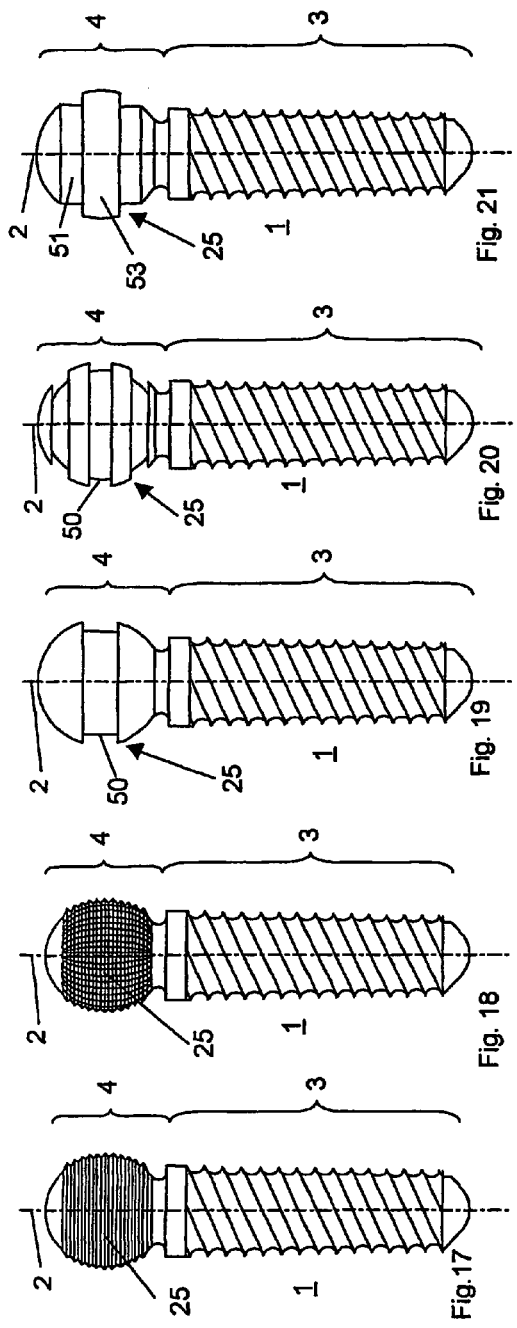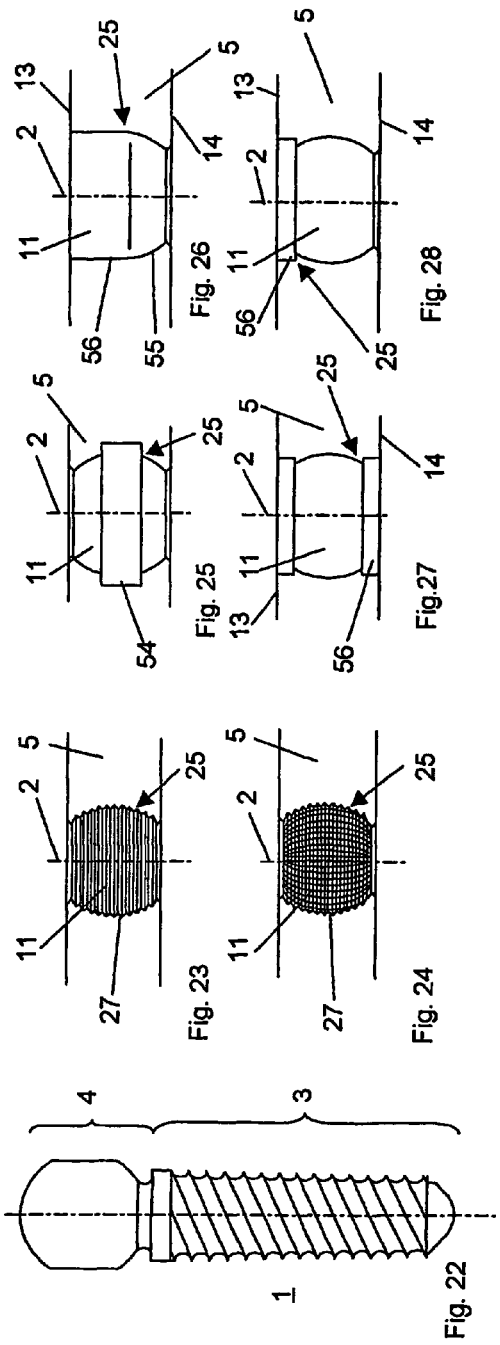

DEVICE FOR THE DYNAMIC FIXATION OF BONES

CROSS-REFERENCE TO RELATED APPLICATION

This is a continuation of pending International Application No. PCT/CH2004/000443, filed Jul. 12, 2004, the entire contents of which are expressly incorporated herein by reference thereto.

FIELD OF THE INVENTION

The invention relates to a device for the dynamic fixation of bones and, more particularly, to an intermediate element of the device for providing a detachable, lockable, ball joint-like connection.

BACKGROUND OF THE INVENTION

The present invention relates to a device for the dynamic stabilization of bones or bone fragments, especially of vertebrae, and comprises at least one longitudinal carrier, which is connected over at least two bone fixation agents attached to vertebral bodies. The bone fixation agents preferably are pedicle screws, which are brought from the rear through the pedicle into the vertebral bodies.

The main indications for a dynamic fixation, especially for one passed through from the rear, are an age-related and/or disease-related degeneration of the integrity of the structure of the spinal column, inflammations, and/or injuries in the region of the intervertebral disk, the ligamentous apparatus, the facet joints, and/or the subchondral bone.

In typical fixation devices, as described in the patents WO 94/00066 (of Schläpfer and Hess), WO 98/25534 (of Schläpfer) and WO 98/52482 (Schläpfer and Hess), the bone fixation agent is connected rigidly with the longitudinal carrier over an interposed connecting element. The connection between the bone fixation agent and the longitudinal carrier is constructed in the form of a ball joint and can be locked in any position. But this means that the fixation device should be fitted anatomically correctly. Moreover, because of this stiffness, these typical fixation devices are used for fusing segments of the vertebrae.

With the stiff connection, the prerequisites are created for a bony fusion of the bridged spinal column segments, but not for a conversion of the movement pattern and stress pattern into one, which reduces the symptoms, promotes the metabolism of the affected structures and is aimed for with the dynamic fixation concept.

A device for the elastically damped connection between the head segments of pedicle screws and a longitudinal carrier is known from the U.S. Pat. No. 5,480,401 of Navas. This known device comprises elastic clamping elements for fixing the spherical head segments of the pedicle screws within the stabilizing device. It is a disadvantage of this known device that the head segment is clamped by friction between the elastic clamping elements, so that the head segment can slip to one side if the torque between the bone fixation agent and the longitudinal carrier is sufficiently high.

The invention is to provide a remedy here.

SUMMARY OF THE INVENTION

An object of the invention is to provide a device for the dynamic fixation of impaired spinal column segments, which, with respect to at least one of the three axes, which are disposed perpendicularly to one another, permits a positive connection, which has damping properties, between the bone fixation agent and the longitudinal carrier.

A distinguishing feature of the invention is the connection between the longitudinal carrier and the bone fixation agent in that the part, forming the connection, has an intermediate element in the region of its connection with the bone fixation agent. Together with the connecting part or together with the head segment of the bone fixation agent, this intermediate element forms a connection, which permits a ball joint-like movement in the unfastened state and forms a low-stress, flexible engagement in the fastened state. These properties are determined by the geometry and material of the intermediate element.

Other distinguishing features of the invention are defined in claims 2-35.

The advantages, achieved by the invention, can be seen to lie essentially therein that, due to the inventive device,

- the ball joint-like connection can be locked positively in any position, in that the structuring at the head segment or at the hollow space wall is pressed into the wall of the counter-piece;
- the connection between the bone fixation agent and the longitudinal carrier has the desired damping properties in spite of the positive locking of the head segment in the intermediate element;
- there is no sliding motion between the joint parts, and the dynamization is based strictly on the elastic deformation of the intermediate element; and
- a controlled stiffness when subjected to shear and rotation, that is, in the case of movements, which can lead to complaints and pain due to degenerative changes in segments of the spinal column, is attainable.

The connection between the longitudinal carrier and the bone fixation agent, which is formed by the connecting part of the invention, can be divided into a connection between the longitudinal carrier and the connecting part and a connection between the connecting part and the bone fixation agent.

The connection between the connecting part and the longitudinal carrier is constructed monoaxially, that is, this connection, when in the unfastened state, permits the connecting part to be shifted longitudinally along the longitudinal carrier and to be rotated about the longitudinal carrier.

In the unfastened state, the connection between the connecting part and the bone fixation agent permits a ball joint-like movement between the bone fixation agent and the connecting part and, in the fastened state, forms a positive connection.

Aside from the clamping means for fastening the connections between the connecting part and the longitudinal carrier, as well as between the connecting part and the bone fixation agent, the connecting part contains an intermediate element, which separates the connecting part from the bone fixation agent.

In contrast to the rigid connections for fusing vertebral bodies, where, for optimally locking the ball joint-like connection, the intermediate element advantageously is produced for a dynamic fixation device from a material that is 20% to 50% softer than that of the bone fixation agent and the connecting part, the intermediate element of a dynamic fixation device preferably is made from a super-elastic or visco-elastic material. The connecting part itself and the bone fixation agent advantageously consist of the same hard material as that used for the rigid connections.

In the unfastened state, the ball joint-like movement between the connecting part and the bone fixation agent is formed by the intermediate element and the head segment of the bone fixation agent or by the intermediate element and the connecting part itself. Moreover, at least one of the two complementary zones, determining the ball joint-like movement, should be constructed spherically convex or spherically concave.

When the connection, which is ball joint-like in the unfastened state, is fastened, a positive connection is attained when the zone of the super-elastic or visco-elastic intermediate element becomes spherically convex (combination of intermediate element and connecting part) or spherically concave (combination of intermediate element and head segment of the bone fixation agent) and the corresponding complementary zone of the connection, which is ball joint-like in the unfastened state, is structured (for example, toothed) or aspherical (for example, rotationally symmetrical). In the latter case, the two complementary zones of the connection, which is ball joint-like in the unfastened state, should be in contact over at least three spatially distributed points.

In the event that the zone of the connection, which is ball joint-like in the unfastened state, is structured, the zone being complementary to the intermediate element, a positive connection results during the fastening in that the soft material of the intermediate element is pressed into the structuring.

A mechanically improved positive connection results if the zone of the ball joint-like connection, which is complementary to the intermediate element, is constructed aspherically. In this case, the geometry of the intermediate element, which is spherical in the unfastened state, adapts to the aspherical geometry of the complementary zone. If, for example, the intermediate element is constructed spherically and the connecting element in the contact region is constructed cylindrically, the sphere in the cylindrical borehole becomes partly cylindrical upon being fastened.

Large internal stresses arise in the intermediate element during fastening. Because of these internal stresses, the intermediate element is stiff in its behavior. If the material of the intermediate element is visco-elastic at least partially, the internal stresses, generated during the fastening, decay over time without loss of the positive connection provided that there is sufficient free space into which the visco-elastic material can flow. As the internal stresses decrease, the flexibility of the connection, which is important for the dynamic behavior of the fixation device, increases.

If the intermediate element consists of a super-elastic material (such as Nitinol), the internal stresses do not decay. The magnitude of the internal stresses may, however, be controlled by the design of the alloy. Moreover, because of the super-elastic behavior of the material, the connection after fastening has a flexibility, which remains constant within a certain load range.

In a different embodiment, the intermediate element is produced from a visco-elastic material, such as a polycarbonate-urethane. Depending on the viscosity of this visco-elastic material, a more or less rapid reduction in the stresses, which have arisen in the connection during the locking of the ball joint, takes place over time in that the visco-elastic material, which is under pressure, can creep into the free spaces, the design of which is planned especially and which support the positive connection. With that, the advantage may be that, due to the decay of the internal stresses arising during the locking of the ball joint, the in situ creates positive connection gains in strength and elasticity.

If the intermediate element is built up at least partially from a visco-elastic material, it is possible to modify the damping properties and the elastic behavior of the ball joint-like connection by modifying the viscosity of the material. The higher the viscosity of the material, the more elastic is the behavior of the ball joint-like connection under normally occurring brief stresses, and the smaller is the damping component.

A more elastic behavior is ideal under normally occurring brief stresses and a more viscous behavior is ideal in the long run for decaying the internal stresses for optimally utilizing the flexibility of the material.

Three-dimensional, macroscopic structuring may be realized, for example, as follows:
  by at least partially annular elevations, which are concentric with the central axis of the bone fixation agent and preferably are peripherally pointed;
  and by a groove extending at least partially peripherally on the convex or concave part of the joint;
  by several grooves extending at least partially peripherally on the convex or concave part of the joint;
  by a flattening extending at least partially peripherally on only convex or concave part of the joint;
  by an at least partially cylindrical construction of the zone, complementary to the intermediate element, of the ball joint-like connection with; in the event of the joint combination between the intermediate element and the connecting part, the zone, which is complementary to the intermediate element, is at least partially in the shape of a hollow cylinder;
  by pyramidal or conical elevations on the convex or concave contact zone; and/or
  by staggered alternate angle teeth or knurling of the convex or concave contact zone.

In further embodiments, the elevations have a height of between 0.5 mm and 1.5 mm and preferably of between 0.8 mm and 1.2 mm. With that, the advantage can be attained that the plastic deformation, that is, the creep of the wall material in the region of the content zone A can be optimized, so that, on the one hand, the broadest possible geometric connection between the active joint parts can be attained and, on the other, the relaxation of the material is adequate.

The fastening of the intermediate element can be realized as follows:
  by a conical connection, which can be wedged by means of the clamping means, between the outer wall of the intermediate element and the wall of the cavity in the connecting part, the clamping means being able to press directly or, by means of an intermediate piece and/or the longitudinal carrier, indirectly onto the intermediate element or
  by a conical connection, which can be wedged by means of the clamping means between the surface of the head segment of the bone fixation agent and the wall of the hollow space, disposed in the intermediate element, the clamping means pressing directly or indirectly onto the intermediate element.

Screws or nuts, which can be connected with the connecting part or the head segment, may be used as clamping means.

The path of the clamping means during the fastening of the device is limited preferably mechanically to a fastening distance S, so that the fastening can be controlled.

BRIEF DESCRIPTION OF THE DRAWINGS

The invention and further developments of the invention are explained in even greater detail with respect to the following partially diagrammatic representations of several examples, in which:

FIG. 6 shows a further embodiment of the section marked A in FIG. 5;

FIG. 7 shows a further embodiment of the section marked A in FIG. 5;

FIG. 8 shows a further embodiment of the section marked A in FIG. 5;

FIG. 9 shows yet a further embodiment of the section marked A in FIG. 5;

FIG. 10 shows a different embodiment of the section marked A in FIG. 5;

FIG. 11 shows a further embodiment of the section marked B in FIG. 4;

FIG. 12 shows a further embodiment of the section marked B in FIG. 4;

FIG. 13 shows a further embodiment of the section marked B in FIG. 4;

FIG. 14 shows yet a further embodiment of the section marked B in FIG. 4;

FIG. 15 shows a different embodiment of the section marked B in FIG. 4 of the inventive fixation device in the unfastened state;

FIG. 16 shows a section of the embodiment of the inventive fixation device, represented in FIG. 15, in the fastened state;

FIG. 17 shows a bone fixation agent of an embodiment of the inventive device;

FIG. 18 shows a bone fixation agent of a different embodiment of the inventive device;

FIG. 19 shows a bone fixation agent of yet another embodiment of the inventive device;

FIG. 20 shows a bone fixation agent of a further embodiment of the inventive device;

FIG. 21 shows a bone fixation agent of yet another embodiment of the inventive device;

FIG. 22 shows a bone fixation agent of a different embodiment of the inventive device;

FIG. 23 shows a development of the cavity in the connecting part of an embodiment of the inventive device;

FIG. 24 shows a development of the cavity in the connecting part of a different embodiment of the inventive device;

FIG. 25 shows a development of the cavity in the connecting part of yet another embodiment of the inventive device;

FIG. 26 shows a development of the cavity in the connecting part of a further embodiment of the inventive device;

FIG. 27 shows a development of the cavity in the connecting part of a yet a further embodiment of the inventive device; and FIG. 28 shows a development of the cavity in the connecting part of a different embodiment of the inventive device.

DETAILED DESCRIPTION OF THE INVENTION

Figure 1:
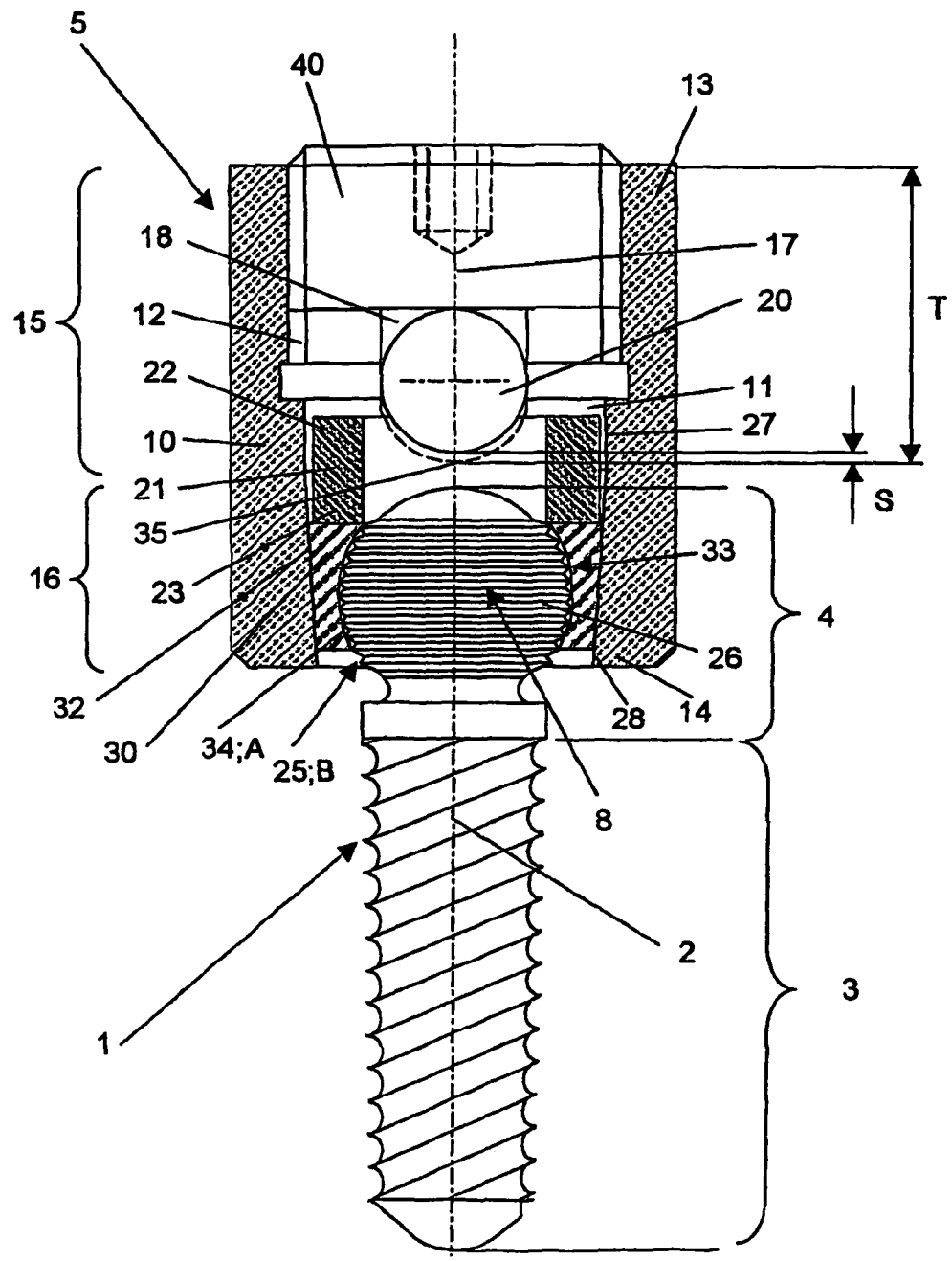
FIG. 1 shows a section through a connecting part between a pedicle screw or a pedicle hook and a longitudinal carrier within an embodiment of the inventive fixation device.

FIG. 1 shows an embodiment that includes a bone fixation agent 1 in the form of a pedicle screw having a central axis 2 and a connecting part 5 in the form of a tube 10 for connecting the bone fixation agent 1 with a longitudinal carrier 20. The bone fixation agent 1 has a coaxial anchoring segment 3, which is configured as the shaft of a screw. The fixation agent 1 also has a head segment 4, which is also disposed coaxially and adjoins the screw shaft at the top. Before it is fixed in the connecting part 5, the longitudinal carrier 20 is placed in a channel 18 disposed in the connecting piece 5 and subsequently fixed by means of the clamping means 40. The channel 18 passes through the connecting part 5 transversely to the central axis 2 and is open at the upper end 13 of the connecting part 5. The ball joint 8 is formed between the connecting part 5 and the bone fixation agent 1 by the intermediate element 30 and the head segment 4, the wall 34 of the cavity 33 in the intermediate element, which forms concave contact zone A, and the outer surface of the head segment 4, which forms convex contact zone B.

The head segment 4 of the bone fixation agent 1 is constructed spherically and is provided with macroscopic, three-dimensional structuring. In the embodiment represented here, the macroscopic structuring 25 is realized by annular elevations 26 disposed concentrically with the central axis 2 of bone fixation agent 1. The annular elevations 26 are constructed triangularly in cross section, so that the shape edges of the elevations 26 can dig into the visco-elastic material of the intermediate element 30.

The connecting element 5 comprises a longitudinal axis 17, an upper end 13 intersecting the longitudinal axis 17, a lower end 14 intersecting the longitudinal axis 17, and a cavity 11, which passes through the connecting part 5 coaxially from the upper end 13 to the lower end 14. The cavity 11 has two segments 15 and 16, which are disposed axially behind one another. Of these, the upper segment 15 surrounds a coaxial cylindrical borehole, in which the radially elastically deformable intermediate element 13 is mounted axially displaceably, whereas the lower segment 16 is constructed so as to taper conically towards the lower end 14. The outer wall 32 of the intermediate element 30 is configured conically so as to be complementary to the inner cone 28 in the lower segment 16, so that the intermediate element 30, when pressed into cavity 11 coaxially against the lower end 14 of the connecting part 5, is pressed radially. Moreover, the intermediate element 30 surrounds an axially continuous open hollow space 33, which is constructed spherically so as to be complementary to the head segment 4 of the bone fixation agent 1. In the decompressed state of the intermediate element 30, the head segment 4 can be snapped from the lower end 14 of the connecting part 5 into the hollow space 33. In the compressed state of the intermediate element 30, the head segment 4 is locked in the hollow space 33. Because of the spherical configuration of the head segment 4 and of the hollow space 33, the bone fixation agent 1 can be swiveled polyaxially relative to the connecting part 5 and also locked at different angles between the longitudinal axis 2 of the bone fixation agent 1 and of the longitudinal axis 17 of the connecting part 5.

During the radial compression of the intermediate element 30, the elevations 26 of the macroscopic structuring 25 at the head segment 4 of the bone fixation agent 1 are pressed into the wall 34 of the hollow space 33. The material of the intermediate element 30 is selected so that, under the forces that arise during the radial compression, it commences to flow and the wall 34 of the hollow space 33 is deformed plastically complementarily to the macroscopic structuring 25. By these means, a positive connection can be attained between the head segment 4 of the bone fixation agent 1 and the intermediate element 30.

The device is shown here in the state in which it is unfastened, so that the head segment 4 is mounted so that it still can rotate freely in the hollow space 33 of the intermediate element 30. The intermediate element 30 can be fastened with clamping means 40 on a fastening distance S until the longitudinal carrier 20 rests on the lower end 35 of the channel 18. During the fastening, the visco-elastic material of the intermediate element 30 is pressed into the three-dimensional structuring 25. After the fastening, the stressors in the intermediate element 30 decay by way of cold flow.

The intermediate element 30 is displaced axially here by means of the clamping means 40, which is configured as a locking screw and can be screwed into an internal thread 12 in the upper segment 15 of the cavity 11 complementary to the thread of the clamping means 40. As it is being tightened, the clamping means 40 presses on the longitudinal carrier 20 inserted in the channel 18. So that, when the clamping means 40 are tightened, the head segment 4 of the bone fixation agent 1 as well as the longitudinal carrier 20 can be fixed in the connecting part 5, an annular connecting piece 21 is disposed between the longitudinal carrier 20 and the intermediate element 30. The depth T of the channel 18 is selected so that the longitudinal carrier 20, placed in the channel 18, presses on the upper end 22 of the connecting piece 21. The lower end 23 of the connecting piece 21 rests on the intermediate element 30. As the clamping means 40 are tightened, the intermediate element 30 presses onto the longitudinal carrier 20, which, together with the adjoining connecting piece 21 and the intermediate element 30 adjoining the connecting piece 21, is pressed against the lower end 14 of the connecting part 5. The conical intermediate element 30 is compressed radially by the conically constructed lower segment 16 of the connecting part 5 and the head segment 4 of the bone fixation agent 1 is locked in the hollow space 33 of the intermediate element 30.

Figure 2:
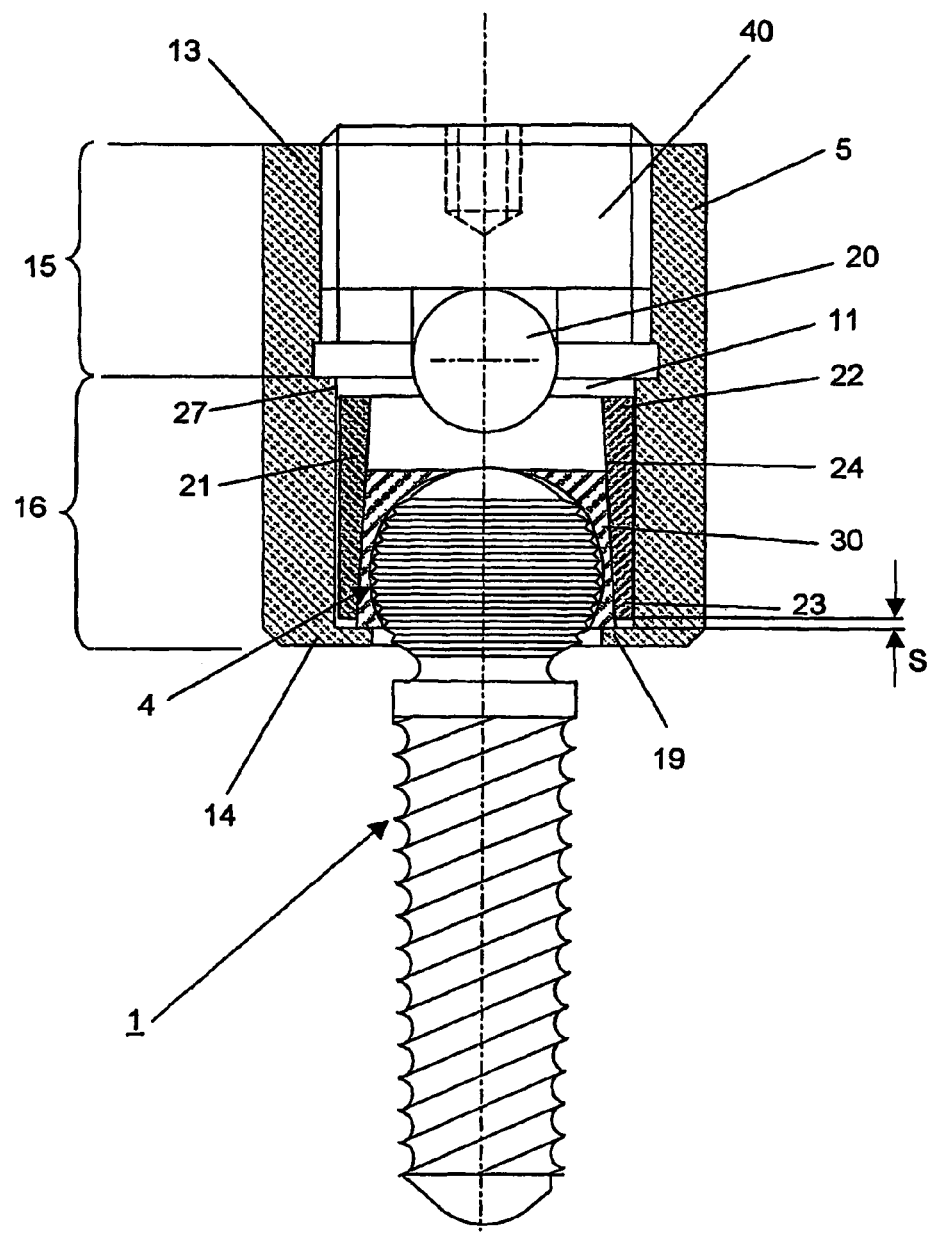
FIG. 2 shows a section through a connecting part between a pedicle screw and a longitudinal carrier within a different embodiment of the inventive fixation device.

FIG. 2 shows an embodiment that differs from that shown in FIG. 1 only in that the lower segment 16 of cavity 11 in connecting part 5 is constructed circularly cylindrically and the connecting piece 21 has an internal cone 24, which expands in the direction of lower end 23 of connecting piece 21, and the intermediate element 30, tapering on the outside in the direction of the upper end 13 of the connecting part 5, is constructed complimentarily conically, so that, when the clamping means 40 are tightened, it presses once again onto the longitudinal carrier 20, which, together with the adjoining intermediate piece 21, is pressed against the lower end 14 of the connecting piece 5. The intermediate element 30, which is complementarily conical on the outside, is compressed radially by the internal cone 24 and the head segment 4 of the bone fixation agent 1 is locked in the hollow space 33 of the intermediate element 30. Here also, the device is shown in the unfastened state. The intermediate element 30 can be fastened until the fastening distance S is overcome and the connecting piece 21 rests on the shoulder 19 at the lower end 14 of the connecting part 5.

Figure 3:
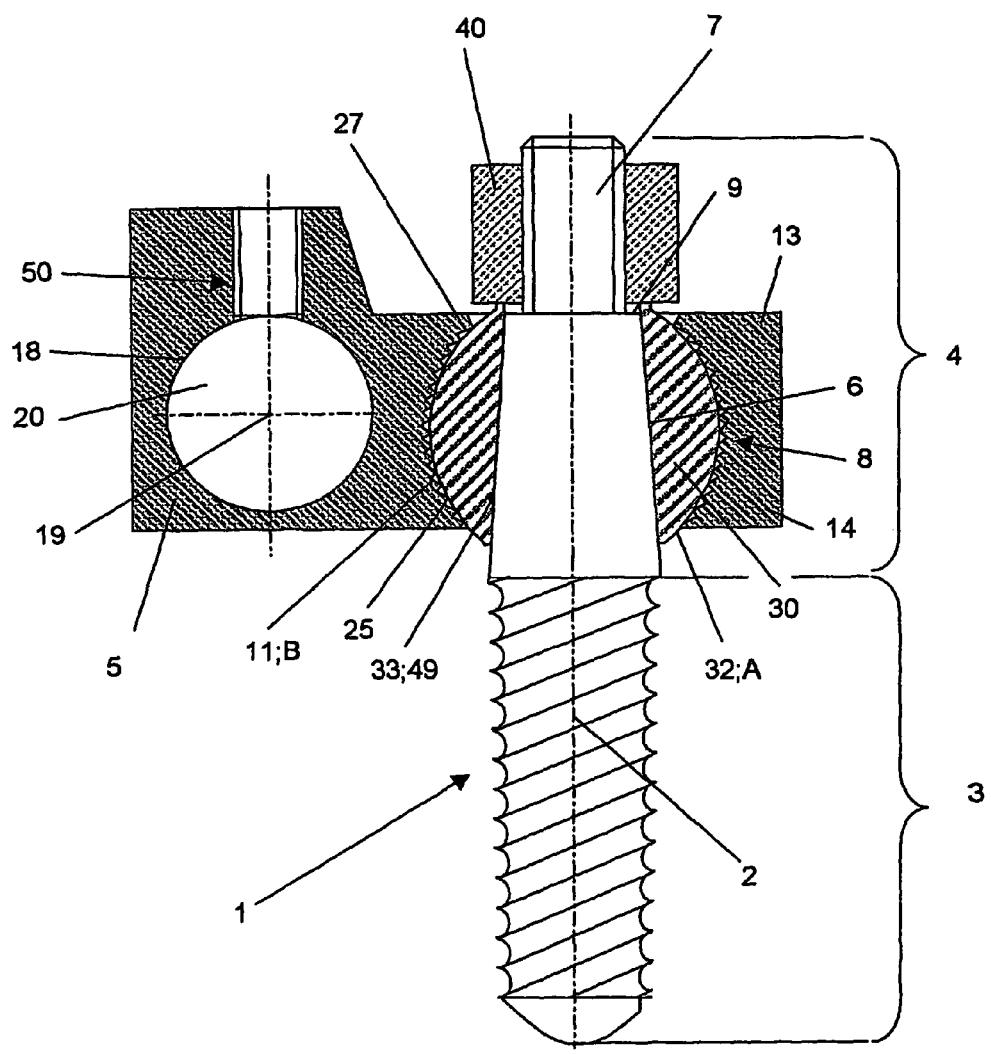
FIG. 3 shows a section through a connecting part between a pedicle screw and a longitudinal carrier within a further embodiment of the inventive fixation device.

FIG. 3 shows an embodiment for which the fixing of longitudinal carrier 20 and the locking of head segment 4 of bone fixation agent 1 take place independently of one another. The ball joint 8 between the connecting piece 5 and the bone fixation agent 1 is formed here by connecting part 5 of intermediate element 30, the wall 27 of the cavity 11 forming the concave contact zone B, and the outer wall 32 of the intermediate element 30 forming the convex contact zone A. Connecting part 5 surrounds a channel 18, which does not intersect the cavity 11, and a fixation means 50, which can be screwed transversely to the channel axis 19 into the channel in order to fix the longitudinal carrier 20 and which is constructed here as a locking screw. Here also, the channel 18 passes through the connecting part 5 transversely to the central axis 2 of the bone fixation element 1 and is closed at its periphery. The spherical cavity 11 is disposed next to the channel 18. The macroscopic structuring 25 is produced here in the wall 27 of the cavity 11. On the outside, the intermediate element 30 is constructed complementarily spherically to the cavity 11, whereas the hollow space 33 of the intermediate element 30 is constructed as a conical central borehole 49, which expands from the upper end 13 of the connecting part 5 to the lower end 14 of the connecting part 5. The head segment 4 of the bone fixation agent 1 encloses a cone 6 here, which is complementary to the central conical borehole 49 and, terminally, a threaded shaft 6, over which the locking means 40, constructed here as a nut, can be screwed. The longitudinal carrier 20 is fixed in the channel 18 independently of the operation of the locking means 40 by means of the fixation means 50. Here also, the device is shown in the unlocked state. The intermediate element 30 can be fastened until the fastening distance S is covered and the locking means 40 rests on the shoulder 9 between the cone 6 and the threaded shaft 7.

When they are tightened, the locking means 40 press at the upper end 13 of the connecting part 5 onto the intermediate element 30, which has been introduced into the cavity 11, and pull the cone 5 at the head segment 4 of the bone fixation agent 1 into the intermediate element 30 in the hollow space 33 formed as a conical central borehole. Due to the wedge action of the cones, which are pressed into one another, the intermediate element 30 is expanded radially and pressed with its outer wall 32 again the wall 27 of the cavity 11, which has been provided with the macroscopic structuring 25. During the radial expansion of the intermediate element 30, the material at the outer wall 32 of the intermediate element 30 commences to flow, so that the outer wall 32 of the intermediate element 30 is deformed plastically by the macroscopic structuring 25 at the wall 27 of cavity 11 and a positive connection is formed between the outer wall 32 of the intermediate element 30 and the wall 27 of cavity 11.

Figure 4:
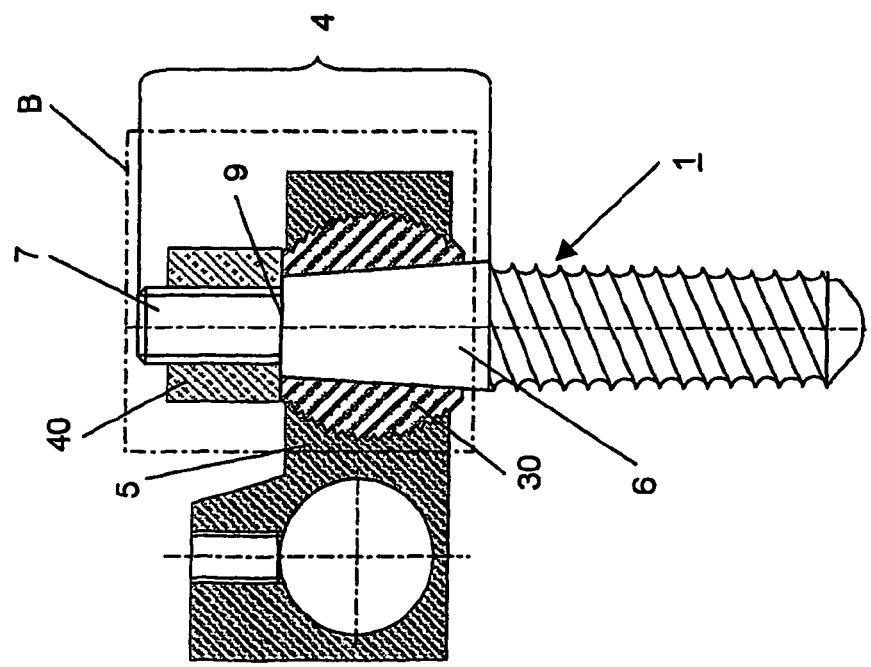
FIG. 4 shows a section through the embodiment of FIG. 3 in the fastened state.

FIG. 4 shows the embodiment of FIG. 3 after locking means 40 has been fastened. Locking means 40 is then resting on shoulder 9 between cone 6 and the threaded shaft.

Figure 5:
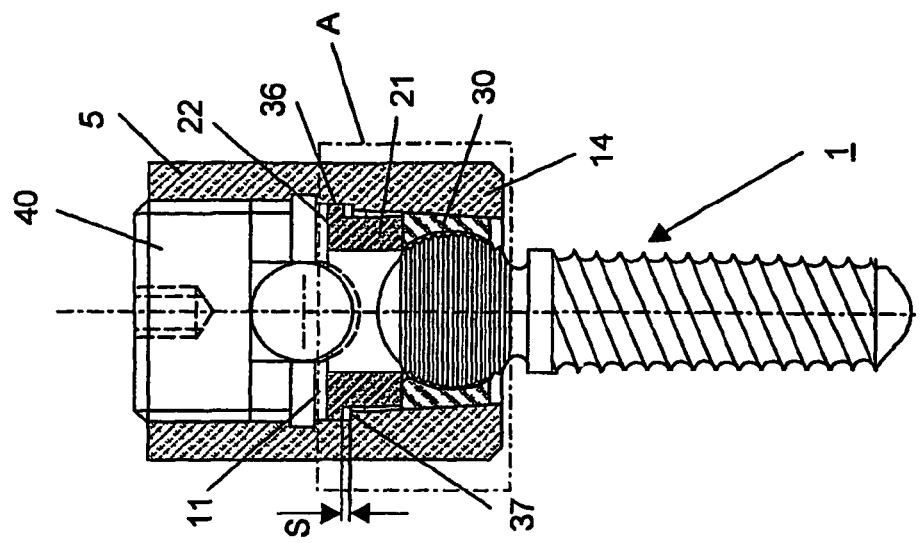
FIG. 5 shows a section through yet another embodiment of the inventive fixation device.

FIG. 5 shows an embodiment that differs from the one shown in FIG. 1 only in that the connecting piece 21, at its upper end 22, has a collar 36, which can be brought to rest on a surface 37 formed by the constriction between the upper segment 15 and the lower segment 16 of the cavity 11. When locking means 40 is tightened, the connecting piece 21 is pressed against the lower end 14 of the connecting part 5 until the collar 36, after covering the fastening distance S, rests on the surface 37. With that, the deformation of the intermediate element 30 is limited to a desired amount, so that the elastic deformability after the relaxation of the intermediate element 30 is not limited.

FIGS. 6 and 7 show embodiments of the inventive device that include intermediate elements 30, the outer walls 32 of which converge conically in the direction of lower end 14 of connecting part 5. Analogous to the embodiment shown in FIG. 5, the embodiment shown in FIG. 6 comprises a cavity 11, the wall 27 of which has a bearing surface 37, which is adjacent to the internal cone 28 and is disposed perpendicularly to and concentric with the central axis 2. In the fastened state of the device, the expanded segment 36 of the connecting piece 21, which is disposed at the upper end 22 of the connecting piece 21, comes to rest against this bearing surface 37. As the device is fastened with locking means 4 (FIG. 1), the connecting piece 21 (FIG. 6) presses with its lower end 23 on the intermediate element 30, so that the latter is pressed axially into the internal cone 28 and, due to the thereby resulting wedge action, is squeezed radially against the head segment 4 of the bone fixation agent 1 (FIG. 1).

The embodiment shown in FIG. 7 differs from that shown in FIG. 6 only in that a locking screw 41, which presses directly onto the intermediate element 30, is provided instead of the connecting piece 21 (FIG. 6), which can be shifted axially in the cavity 11. The locking screw 41 is screwed into an internal thread 42, which is cut into wall 27 of cavity 11 at its longitudinal section adjoining internal cone 28. As the locking screw 40 is tightened, it presses with its front side, which is directed towards the lower end 14 of the connecting part 5, onto the intermediate element 30, so that the latter is pressed axially into the internal cone 28 and squeezed by the resulting wedge action radially against head segment 4 of bone fixation agent 1 (FIG. 1). At its end, directed against the upper end 13 of the connecting part 5, the locking screw 41 is provided with receiving slot 43 for a screw driver.

The embodiment shown in FIG. 8 differs from that shown in FIG. 6 only in that cavity 11 does not have an internal cone 28 and, instead, is constructed circularly cylindrically and has a constriction 19 at the lower end 14 of the connecting part 5. The intermediate element 30 has an outer wall 32, which is complementary to the cavity 11 and is provided at its face surfaces, which are perpendicular to the central axis 2, with concentric, conical depressions 44. As the device is fastened by means of the locking means 40, the connecting piece 21 presses with its lower end 3 onto the face surfaces of the outer wall 32, which are tapered by the conical depressions 44, so that the connecting piece is squeezed axially and, with that, also radially against head segment 4 of bone fixation agent 1 (FIG. 1). The intermediate element 30 could also be fastened in a manner similar to that shown in FIG. 7.

The embodiment shown in FIGS. 9 and 10 differs from the embodiments shown in FIGS. 6 and 7 only in that cavity 11 does not have an internal cone 28 and, instead, is constructed circularly cylindrically and has a constriction 19 at the lower end 14 of the connecting part 5. An undercut 46, into which a complementary expansion 45 at the intermediate element 30 is inserted, so that the intermediate element 30 is secured to prevent movements parallel to the central axis 2, is disposed between the constriction 19 and the wall 27 of cavity 11. Moreover, the outer wall 32 of the intermediate element 30 tapers with an external cone 48 in the direction of the upper end 13 (FIG. 1) of the connecting part 5. The connecting piece 21 (FIG. 9) or the locking screw 41 (FIG. 10) is provided with a borehole segment 47, which expands in a complementary manner, so that, as the device is fastened, the intermediate element 30 with the conical borehole segment 47 is shifted over the outer cone 48 and, consequently, the intermediate element 30 is squeezed radially. The fastening of the ball joint-like connection between the intermediate element 30 and the head segment 4 of the bone fixation agent 1 (FIG. 1) takes place, in the case of the embodiment shown in FIG. 9, in a manner similar to that of the embodiment shown in FIG. 6 and, in the case of the embodiment shown in FIG. 10, in a manner similar to that shown in FIG. 7.

Different embodiments of the intermediate element 30 and of the locking means 40 are shown in FIGS. 11 to 16. They differ from the embodiment shown in FIG. 3 as follows:
  the locking means 40 are realized by a screw 24, which can be screwed into a complementary internal thread 31, which has been cut in a terminal, open borehole 29 in head segment 4. As the locking means 40 are fastened, the conical head segment 4 of bone fixation agent 1, as in the embodiment shown in FIG. 3, is pulled into the complementarily constructed hollow space 33 in the intermediate element 30, so that the intermediate element 30 is expanded and pushed against the wall 27 of cavity 11 (FIG. 11);
  the locking means 40 are realized by a centrally drilled cone 38 and a terminal nut 39, which can be screwed over the threaded shaft 7. The tapered end of the centrally drilled cone 38 is pushed forward against the anchoring segment 3 of the bone fixation agent 1 in the complementarily constructed hollow space 33 in the intermediate element 30 and wedged by means of the nut 39 (FIG. 12);
  the locking means 40 differ from those of the embodiment, shown in FIG. 3 only in that the cone 6 at the head segment 4 of the bone fixation agent 1 is shortened and a centrally drilled cone 38 is pushed with its tapered end directed against the cone 6 over the screw shaft 7 into the complementary, doubly conical hollow space 33 in the intermediate element 30. By means of the locking means 40, constructed as a nut 39, the two cones 6; 38 are wedged in the hollow space 33 (FIG. 13).
  the locking means 40, shown in FIG. 14, differ from the embodiment, shown in FIG. 13, only in that, instead of the threaded shaft 7 (FIG. 13), a coaxial, terminal, open borehole 29 with an internal thread 31 is disposed at the head segment 4 of the bone fixation agent 1, so that the locking means 40, constructed as the screw 24, can be screwed terminally into the head segment 4, so that the cones 6; 38 can be wedged;
  the cavity 11 in the connecting part 5 is not constructed complementarily spherically to the outer wall 32 of the intermediate element 30 (FIG. 3) and, instead, has at least partially the shape of a hollow cylinder (FIGS. 15; 16). The locking means 40 are equipped as in the embodiment shown in FIG. 11. In the unfastened state of the device (FIG. 15), the wall 27 of the cavity 11 and the outer wall 32 of the intermediate element 30, which form the contact zones A; B of the ball joint-like connection, should be in contact at least over three spatially distributed points. As the device is fastened, the geometry of the intermediate element 30, which is spherical in the unfastened state, adapts to the aspherical geometry of the wall 27 of the cavity 11. In the fastened state of the device (FIG. 16), the intermediate element 30 then has a partially cylindrical shape, so that a positive connection is established between the connecting part 5 and the intermediate element 30.

FIGS. 17 to 22 show different embodiments of bone fixation agent 1 that are constructed, by way of example, as pedicle screws with a screw shaft as anchoring segment 3 and an essentially spherical screw head as head segment 4. The bone fixation agents 1 shown differ due to the construction of the three-dimensional structuring 25, the structuring 25:
  being configured as toothing in FIG. 1;
  being configured as staggered alternating angle teeth in FIG. 18;
  being constructed as a circular, peripheral groove 50, which is concentric with the central axis 2 in FIG. 19;
  comprising three circular grooves 50 in FIG. 20, which are concentric with the central axis 2;
  comprising two circularly cylindrical segments 51 in FIG. 21, which are axially adjacent to a spherical of zone 53, which is disposed axially centrally; or
  comprising two diametrically opposite lateral surfaces 52 in FIG. 22.

Different embodiments of the cavity 11 in the connecting part 5 of FIG. 3 are shown in FIGS. 23 to 28. For each embodiment, the cavity 11, which is concentric with the central axis 2, has a different three-dimensional structuring 25,
  the cavity 11 in FIG. 23 being constructed in the form of a hollow spherical zone and having toothing as the structuring 25 at its wall 27, the cavity 11 in FIG. 24 being constructed in the form of a hollow spherical zone and having staggered alternate angle teeth at its wall 27, the cavity 11 in FIG. 25 being constructed in the form of a hollow spherical zone and having a circular peripheral undercut 54, concentric with the central axis 2, the cavity 11 in FIG. 26 comprising a first segment 56, which is in the form of a hollow spherical zone, and a second segment 56, which is in the form of a hollow circular cylinder, the segment 55, which is in the form of a hollow spherical zone, being disposed between the lower end 14 of the connecting part 5 and the great circle of the cavity 11, which is perpendicular to the central axis 2, and the segment 56, which is in the form of a hollow, circular cylinder, being disposed between the upper end 13 of the connecting part 5 and the segment 55, which is in the form of a hollow spherical zone, the cavity 11 in FIG. 27 being constructed centrally in the form of a hollow spherical zone and encompassing a hollow cylindrical segment 56 adjoining the upper end 13 and the lower end 14 of the connecting part 5 the cavity 11 in FIG. 28 differing from that in FIG. 27 only in that one hollow cylindrical segment 56, adjoining the upper end 13 of the connecting part 5, is provided.

The present invention has been described in connection with the preferred embodiments. These embodiments, however, are merely for example and the invention is not restricted thereto. It will be understood by those skilled in the art that other variations and modifications can easily be made within the scope of the invention as defined by the appended claims, thus it is only intended that the present invention be limited by the following claims.

What is claimed is:

1. A device for the dynamic fixation of bones or bone fragments, including segments of the spinal column, the device comprising:
    at least one bone fixation agent having a central axis, an anchoring segment operative to be anchored at or in a bone, and an axially adjoining head segment;
    a connecting part having a longitudinal axis, a cavity coaxial with the longitudinal axis defining an inner surface, and a channel transverse to the longitudinal axis operative to accommodate a longitudinal carrier, the cavity having an upper portion and a lower portion, the inner surface of the lower portion having a shape, the connecting part suitable for the detachable connection of the bone fixation agent and the longitudinal carrier;
    an at least partially deformable intermediate element operatively associated with the head segment for coupling the bone fixation agent and the connecting part, the intermediate element at least partially manufactured from a visco-elastic material and has an outer surface, the intermediate member being receivable within the lower portion of the cavity of the connecting part; and
    a locking means operative to deform, either directly or indirectly, the intermediate element, wherein the outer surface of the visco-elastic portion of the intermediate element and the inner surface of the connecting part comprise contact zones A, B which are in contact with one another,
    wherein in the unfastened state the outer surface of the contact zone A of the intermediate element has a shape that is non-corresponding and different than the shape of the contact zone B of the inner surface of the lower portion of the cavity of the connecting part in which the intermediate element is received, and a ball joint-like movement between the connecting part and the bone fixation agent is permitted, and in the fastened state the bone fixation agent is flexibly connected to the connecting part such that the bone fixation agent is permitted to move relative to the connecting part via elastic deformation of the intermediate member, and the intermediate element at least partially changes shape.

2. The device of claim 1 wherein the two contact zones A, B, forming a ball joint-like connection in the unfastened state, are in contact with one another at least at three points distributed in space.

3. The device of claim 1 wherein the two contact zones A, B, which form a ball joint-like connection in the unfastened state, contact one another at least partly on an outline of a circle.

4. The device of claim 1 wherein the contact zone B, in contact with the contact zone A, which is disposed at the intermediate element, is toothed at least in the area of contact.

5. The device of the claim 1 wherein the contact zone B, in contact with the contact zone A in the unfastened state, which is disposed at the intermediate element, is constructed rotationally symmetrically in the area of contact.

6. The device of claim 1 wherein the intermediate element has a spherical outer wall and the cavity is constructed as a borehole coaxial with the central axis.

7. The device of claim 6 further comprising, in the area of the cavity between the intermediate element and the connecting part, a stop that limits movement of the intermediate element relative to the connecting element.

8. The device of claim 1 wherein the contact zone B, which is in contact with the contact zone A that is disposed at the intermediate element, has at least one groove in the contact region.

9. The device of claim 1 wherein the contact zone B, in contact with the contact zone A that is disposed at the intermediate element, has a spherical zone with at least one axially, terminal, circularly cylindrical segment or, in the contact region, a hollow sphere-like segment with at least one axially terminal, hollow, circularly cylindrical segment.

10. The device of claim 1 wherein the visco-elastic material comprises an elastic-visco-elastic material.

11. The device of claim 1 wherein the visco-elastic material has a Shore hardness of between 50 A and 90 A.

12. The device of claim 1 wherein the visco-elastic material has a Shore hardness of between 50 D and 90 D.

13. The device of claim 1 wherein the intermediate element includes a concave hollow space for receiving the head segment of the bone fixation agent.

14. The device of claim 13 wherein the head segment is tapered.

15. The device of claim 1 wherein the cavity is concave and suitable for the ball joint-like accommodation of the intermediate element.

16. The device of claim 15 wherein the intermediate element has a convex outer wall.

17. The device of claim 1 wherein the intermediate element comprises a layer of a highly elastic, biocompatible plastic.

18. The device of claim 17 wherein the plastic layer is sprayed onto a surface of the intermediate element.

19. The device of claim 17 wherein the thickness of the layer is between 2 mm and 5 mm.

20. The device of claim 1 wherein the visco-elastic material is manufactured from polycarbonate urethane.

21. The device of claim 1 wherein the locking means is limited mechanically to a fastening distance of S.

22. The device of claim 1, wherein the intermediate element has a spherically convex outer surface in the unfastened state.

23. The device of claim 1, wherein the contact zone B of the ball joint-like connection, which is in contact with the contact zone A at the intermediate element and is located between the connecting part and the bone fixation agent, has a three-dimensional structuring.

24. The device of claim 23, wherein the visco-elastic material of the intermediate element is pressed into the three-dimensional structuring.

25. The device of claim 23 wherein the three-dimensional structuring includes elevations that have a height of 0.5 to 1.5 mm.

26. The device of claim 23 wherein the structuring comprises toothing.

27. The device of claim 23 wherein the structuring comprises pyramidal or conical elevations.

28. The device of claim 1, wherein the visco-elastic intermediate element behaves such that the stresses arising during the fastening fade away over time without loosing the positive connection achieved by operating the locking means.

29. The device of claim 1, wherein in the fastened state the intermediate member adapts at least partially to the shape of the inner surface of the lower portion of the cavity.

30. The device of claim 1 wherein the intermediate member is coupled to the head segment.

31. The device of claim 1 wherein the contact zone B of the connecting part is non-spherically shaped and the contact zone A of the visco-elastic portion of the intermediate member is spherically shaped.

32. The device of claim 31 wherein the inner surface of the contact zone B of the cavity of the lower portion of the connecting part is cylindrically shaped.

33. A device for the dynamic fixation of bones or bone fragments, including segments of the spinal column, the device comprising:

at least one bone fixation agent having a central axis, an anchoring segment operative to be anchored at or in a bone, and an axially adjoining head segment;

a connecting part having a longitudinal axis, a cavity coaxial with the longitudinal axis defining an inner surface, and a channel transverse to the longitudinal axis operative to accommodate a longitudinal carrier, the cavity having an upper portion and a lower portion, the inner surface of the lower portion having a shape, the connecting part suitable for the detachable connection of the bone fixation agent and the longitudinal carrier;

an at least partially deformable intermediate element operatively associated with the head segment for coupling the bone fixation agent and the connecting part, the intermediate element at least partially manufactured from polycarbonate urethane visco-elastic material and the polycarbonate urethane has an outer surface the outer surface portion of the intermediate member being receivable within the lower portion of the cavity of the connecting part; and a locking means operative to defoiin, either directly or indirectly, the intermediate element, wherein the outer surface of the polycarbonate urethane portion of the intermediate element and the inner surface of the connecting part comprise contact zones A, B which are in contact with one another, wherein in the unfastened state the outer surface of the contact zone A of the intermediate member has a shape that is non-corresponding and different than the shape of the inner surface of the lower portion of the cavity of the connecting part in which the intermediate element is received and a ball joint-like movement between the connecting part and the bone fixation agent is permitted, and in the fastened state the bone fixation agent is flexibly connected to the connecting part such that the bone fixation agent is permitted to move relative to the connecting part via elastic deformation of the intermediate member, and the outer surface of the intermediate element contacts the inner surface of the lower portion of the cavity and changes shape and adapts at least partially to the shape of the lower portion of the cavity.

34. The device of claim 33 wherein the inner surface of the lower portion of the connecting part is non-spherically shaped and the outer surface of the visco-elastic portion of the intermediate member received within and which contacts the lower portion of the connecting part is spherically shaped.

35. The device of claim 34 wherein the inner surface of the cavity of the lower portion of the connecting part is cylindrically shaped.

* * * * *